United States Patent
Kawamura et al.

(10) Patent No.: US 10,501,399 B2
(45) Date of Patent: Dec. 10, 2019

(54) LACTIC ACID MANUFACTURING METHOD

(71) Applicant: Toray Industries, Inc., Tokyo (JP)

(72) Inventors: Kenji Kawamura, Kamakura (JP); Miyuki Horiguchi, Kamakura (JP); Satoshi Sakami, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/129,870

(22) PCT Filed: Mar. 30, 2015

(86) PCT No.: PCT/JP2015/059861
§ 371 (c)(1),
(2) Date: Sep. 28, 2016

(87) PCT Pub. No.: WO2015/152127
PCT Pub. Date: Oct. 8, 2015

(65) Prior Publication Data
US 2017/0152204 A1    Jun. 1, 2017

(30) Foreign Application Priority Data

Mar. 31, 2014   (JP) .................................. 2014-072610

(51) Int. Cl.
| | | |
|---|---|---|
| *C07C 51/42* | (2006.01) | |
| *C07C 51/43* | (2006.01) | |
| *C07C 51/44* | (2006.01) | |
| *C08G 63/06* | (2006.01) | |
| *C08G 63/80* | (2006.01) | |
| *C08G 63/08* | (2006.01) | |

(52) U.S. Cl.
CPC .............. *C07C 51/43* (2013.01); *C07C 51/44* (2013.01); *C08G 63/06* (2013.01); *C08G 63/08* (2013.01); *C08G 63/80* (2013.01)

(58) Field of Classification Search
CPC .................................. C07C 59/08; C12P 7/56
See application file for complete search history.

(56) References Cited

U.S. PATENT DOCUMENTS

| | | | |
|---|---|---|---|
| 3,839,408 A | 10/1974 | Arend et al. | |
| 6,489,508 B1 | 12/2002 | Van Gansbeghe et al. | |
| 6,596,901 B1 | 7/2003 | Eck et al. | |
| 6,630,603 B1 * | 10/2003 | Van Breugel | C07C 51/43 |
| | | | 562/580 |
| 2009/0194488 A1 | 8/2009 | Hosotani | |
| 2011/0263811 A1 * | 10/2011 | Sawai | B01D 61/027 |
| | | | 528/272 |
| 2014/0051138 A1 | 2/2014 | Na et al. | |

FOREIGN PATENT DOCUMENTS

| | | | |
|---|---|---|---|
| CN | 101851643 | * | 5/2013 |
| JP | 11-35662 A | | 2/1999 |
| JP | 2000-514077 A | | 10/2000 |
| JP | 2001-506274 A | | 5/2001 |
| JP | 2002-540090 A | | 11/2002 |
| JP | 2005-8526 A | | 1/2005 |
| JP | 2010-189310 A | | 9/2010 |
| WO | 00/56693 A1 | | 9/2000 |
| WO | 2007/129724 A1 | | 11/2007 |
| WO | 2012/147903 A1 | | 11/2012 |

OTHER PUBLICATIONS

Sanglard et al "Poly(lactic acid) Synthesis and Characterization", Chimia 2012, 66, No. 12, pp. 951-954, published on Dec. 2012.*

* cited by examiner

*Primary Examiner* — Gregory Listvoyb
(74) *Attorney, Agent, or Firm* — DLA Piper LLP (US)

(57) ABSTRACT

A method of producing lactic acid includes subjecting a lactic acid-containing solution to distillation to collect lactic acid from the vapor side (Step A); subjecting the lactic acid obtained in Step A to crystallization (Step B); subjecting the lactic acid slurry obtained in Step B to solid-liquid separation into lactic acid crystals and a mother liquor (Step C); and circulating the mother liquor obtained in Step C to Step B (Step D).

21 Claims, 1 Drawing Sheet

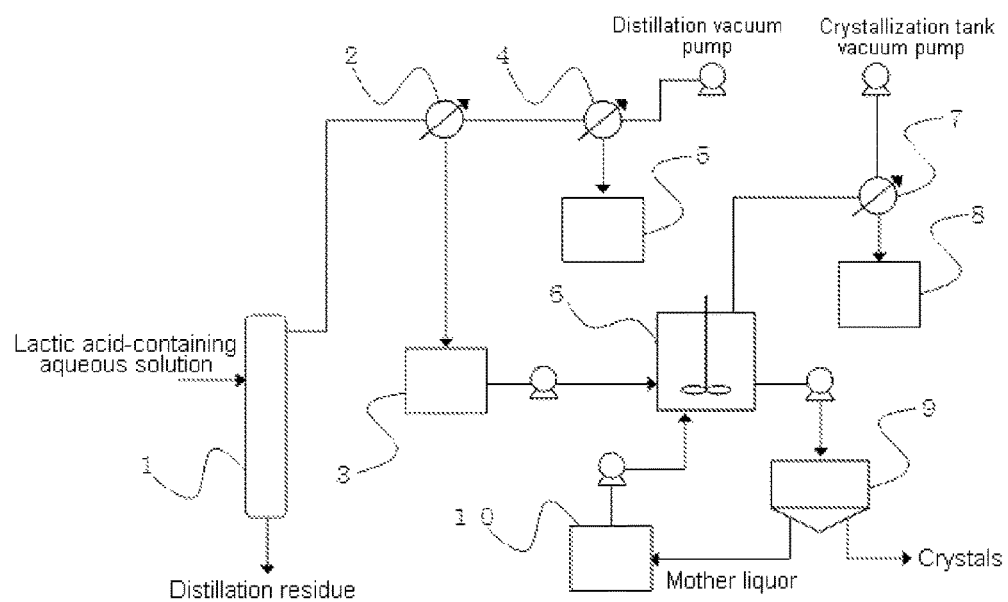

LACTIC ACID MANUFACTURING METHOD

TECHNICAL FIELD

This disclosure relates to a method of isolating and purifying high-purity lactic acid with a high yield from a lactic acid-containing aqueous solution derived by microbial fermentation.

BACKGROUND

Lactic acid is widely applied not only to uses such as food and pharmaceuticals, but also to industrial uses as a monomer material for plastics, and has been increasingly demanded. 2-Hydroxypropionic acid, that is, lactic acid, is known to be produced by microbial fermentation, wherein microorganisms convert substrates containing hydrocarbons such as glucose into lactic acid. Lactic acid is divided into optical isomers, the (L)-isomer and the (D)-isomer, based on the conformation of the substituent bound to the carbon at the a-position of carbonyl. By appropriately selecting the microorganism for microbial fermentation, (L)- or (D)-lactic acid can be selectively produced, or lactic acid as a mixture of the (L)-isomer and the (D)-isomer (racemic body) can be produced.

Production of lactic acid by microbial fermentation is generally carried out while a pH appropriate for the microbial fermentation is maintained by addition of an alkaline substance (e.g., calcium hydroxide) to the culture broth. Most of the lactic acid produced as an acidic substance by the microbial fermentation is present as a lactic acid salt (e.g., calcium lactate) in the culture broth due to the addition of the alkaline substance. In general, when lactic acid is used as monomers for a plastic, the lactic acid is preferably in the free form obtained by adding an acidic substance (e.g., sulfuric acid) to the culture broth after completion of the fermentation. However, the lactic acid fermentation broth obtained by microbial fermentation contains, besides lactic acid as the product of interest, organic acids and salts thereof, proteins, amino acids, and nonionic compounds such as glycerol, as impurities. Thus, when the lactic acid is used as monomers for a plastic, the lactic acid needs to be separated from these impurities.

As a method of removing various impurities from a lactic acid-containing solution derived from a lactic acid fermentation broth obtained by microbial fermentation, and recovering lactic acid, a method based on crystallization of lactic acid is known. In that crystallization, lactic acid is precipitated as crystals to increase the chemical purity as well as the optical purity of the lactic acid, and most of the fermentation-derived impurities are distributed into the liquid component (mother liquor). Since, normally, a large amount of lactic acid remains in the mother liquor together with impurities, industrial-scale production of lactic acid from a lactic acid fermentation broth requires enhancement of the purification yield by recycling of the mother liquor to any of the preceding steps. As an example of purification of lactic acid by crystallization, JP 2010-189310 A discloses a method in which a lactic acid-containing solution is diluted and hydrolyzed, followed by performing crystallization to increase the yield. Japanese Translated PCT Patent Application Laid-open No. 2002-540090 discloses a method in which a lactic acid-containing solution is distilled, and crystallization is then performed to recover high-quality lactic acid. However, those methods do not concretely describe a process of recycling the mother liquor after the crystallization.

It could therefore be helpful to provide a method of efficiently and stably producing highly pure lactic acid by recovering lactic acid from a lactic acid-containing solution by crystallization, and suppressing accumulation of multimeric lactic acid and impurities in the recycle system for the mother liquor.

SUMMARY

We discovered that, in a process of crystallizing and recovering lactic acid from a lactic acid-containing solution while recycling the mother liquor to the crystallization step to recover lactic acid with a high yield, accumulation of multimeric lactic acid and impurities in the recycle system occurs to cause a decrease in the crystallization yield, which is problematic. We then discovered that, in a process of crystallizing lactic acid and recovering purified lactic acid crystals while circulating the mother liquor to the crystallization step, by using lactic acid recovered from the vapor side after distillation of a lactic acid-containing solution as the liquid to be supplied for the crystallization step, accumulation of multimeric lactic acid in the circulation system in the crystallization step can be prevented to allow stable production of lactic acid crystals with a high yield.

We thus provide:

(1) A method of producing lactic acid, comprising the steps of:

subjecting a lactic acid-containing solution to distillation to collect lactic acid from the vapor side (Step A);

subjecting the lactic acid obtained in Step A to crystallization (Step B);

subjecting the lactic acid slurry obtained in Step B to solid-liquid separation into lactic acid crystals and a mother liquor (Step C); and circulating the mother liquor obtained in Step C to Step B (Step D).

(2) The method of producing lactic acid according to (1), wherein the lactic acid-containing solution is derived from microbial fermentation.

(3) The method of producing lactic acid according to (1) or (2), wherein the crystallization in Step B is cooling crystallization, evaporative crystallization, or insulated crystallization.

(4) A method of producing polylactic acid, the method comprising the steps of:

producing lactic acid by the method of producing lactic acid according to any one of (1) to (3); and producing polylactic acid using the lactic acid obtained in the above step as a material (Step E).

(5) The method of producing polylactic acid according to (4), wherein the Step (E) is a step of direct dehydration condensation of the lactic acid.

We thus enable stable production of high-purity lactic acid with a high yield from a lactic acid-containing solution.

BRIEF DESCRIPTION OF THE DRAWING

FIG. 1 is a schematic diagram showing an example of our method.

DESCRIPTION OF SYMBOLS

1. Evaporator
2. Evaporative partial condenser
3. Evaporative partial condensate-receiving tank
4. Evaporative total condenser
5. Evaporative total condensate-receiving tank 6. Crystallization tank
7. Crystallization tank condenser
8. Crystallization condensate-receiving tank
9. Crystallization slurry centrifuge
10. Crystallization mother liquor-receiving tank

DETAILED DESCRIPTION

Our method of producing lactic acid is characterized in that it comprises the steps of:
  subjecting a lactic acid-containing solution to distillation to collect lactic acid from the vapor side (Step A);
  subjecting the lactic acid obtained in Step A to crystallization (Step B);
  subjecting the lactic acid slurry obtained in Step B to solid-liquid separation into lactic acid crystals and a mother liquor (Step C); and
  circulating the mother liquor obtained in Step C to Step B (Step D).

The lactic acid-containing solution is not limited as long as its main component is lactic acid in the free form (hereinafter referred to as free lactic acid). The lactic acid-containing solution is preferably derived from microbial fermentation. The lactic acid-containing solution derived from microbial fermentation may be either a fermentation culture broth itself, or a product prepared by subjecting a fermentation culture broth to a plurality of purification steps.

When the lactic acid-containing solution is derived from microbial fermentation, and an alkaline substance for pH adjustment is added during the microbial fermentation culture, the major component of the lactic acid-containing solution may become a lactic acid salt (more specifically, lithium lactate, sodium lactate, potassium lactate, calcium lactate, magnesium lactate, aluminum lactate, or ammonium lactate, or a mixture of two or more of these). In such cases, a pretreatment is carried out to convert the lactic acid salt in the lactic acid-containing solution to free lactic acid. As a method of obtaining free lactic acid from the lactic acid salt, a method by adding an acidic substance to the lactic acid-containing solution can be employed. The acidic substance is not limited, and sulfuric acid, hydrochloric acid, carbonic acid, phosphoric acid, nitric acid or the like may be used. In view of forming an insoluble salt, thereby allowing easy separation of free lactic acid from the salt, sulfuric acid is preferably used.

When an acidic substance is added to the solution containing a lactic acid salt as a major component to convert the solution to a free lactic acid-containing solution, and the cationic component of the lactic acid salt is removed as an insoluble salt, the free lactic acid-containing solution from which cations derived from the lactic acid salt are removed can be obtained by adding the acidic substance to the lactic acid salt-containing solution and removing the cationic component in the solution as an insoluble salt by performing solid-liquid separation such as precipitation or filtration separation. The method of removing the insoluble salt by solid-liquid separation is not limited, and a method known to those skilled in the art such as filtration through qualitative filter paper or centrifugation may be applied. When a large amount of free lactic acid is contained in the lactic acid fermentation culture broth, for example, when a lactic acid fermentation culture broth obtained by lactic acid fermentation at a low pH (for example, with a pKa of not more than that of lactic acid) is used, the lactic acid fermentation culture broth may be subjected as it is to Step A.

In Step A, the lactic acid-containing solution is subjected to a step of distillation. We discovered that the impurities that can be removed by the distillation step (Step A) include impurities which promote oligomerization (multimerization) of lactic acid, and that, by removing such impurities in the distillation step, accumulation of lactic acid oligomers in the later-described crystallization step (Step B) and mother liquor circulation step (Step D) can be suppressed so that recovery of lactic acid crystals is possible with a high yield by a stable operation. Purification of lactic acid by the distillation step (Step A), which requires heating for evaporation of lactic acid, has been considered to be a cause of oligomerization of lactic acid (see, for example, page 6 of Japanese Translated PCT Patent Application Laid-open No. 2001-506274). In spite of the risk of oligomerization of lactic acid, lactic acid obtained by the distillation step (Step A) is subjected to the later-mentioned crystallization step (Step B). This produces an unexpected result that, as shown in our Examples, accumulation of lactic acid oligomers in the mother liquor circulation step (Step D) can be suppressed compared to when the distillation step (Step A) is not employed.

In the distillation of Step A, a lactic acid-containing solution is subjected to distillation, and lactic acid is recovered from the vapor side, while non-volatile impurities having high boiling points are removed as a distillation residue solution. The lactic acid concentration in the lactic acid-containing solution to be subjected to the distillation step is not limited. When the lactic acid concentration in the solution is too low, a large distillation equipment is necessary, while when the concentration is too high, excessive oligomerization may occur, leading to a low distillation yield. Thus, the distillation can be preferably carried out when the concentration of lactic acid is 40 to 95 wt %, more preferably 60 to 90 wt %. The distillation step is carried out under a reduced pressure of not less than 1 Pa and not more than atmospheric pressure (normal pressure, about 101 kPa). When the step is carried out under a reduced pressure of 10 Pa to 30 kPa, the distillation temperature can be lowered, which is more preferred. The distillation temperature when the step is carried out under reduced pressure is 20° C. to 200° C., but, when the distillation is carried out at a temperature higher than 180° C., racemization of lactic acid may be caused by the influence of impurities. Therefore, the distillation of lactic acid can be preferably carried out at a temperature of 50° C. to 180° C., more preferably 60° C. to 150° C. The distillation step to be applied may be either batch distillation or continuous distillation.

Since lactic acid is likely to undergo oligomerization under dehydration conditions (by heating and/or under reduced pressure) because of its structure, the residence time is preferably as short as possible. Accordingly, a film evaporator such as a falling-film evaporator or wiped film evaporator is preferably used as the evaporator since it enables achievement of a reduced distillation time and can therefore increase the recovery of lactic acid. The lactic acid vaporized by the evaporator is recovered by cooling in a condenser. Since the vapor phase contains not only lactic acid, but also water and low boiling components, a plurality of condensers may be used such that, for example, lactic acid and, in some cases, an arbitrary proportion of water are condensed in the first-stage condenser, and the remaining water and low boiling components are condensed in the second-stage condenser.

When the concentration of the lactic acid-containing solution to be subjected to Step A is low, lactic acid is preferably concentrated prior to Step A. The method of concentrating the lactic acid-containing solution may be a common method known to those skilled in the art, and examples of the method include methods using a reverse osmosis membrane, and concentration under heat using an evaporator (evaporation method). Two or more of these methods may be used in combination.

A reverse osmosis membrane is also called an RO membrane. Since reverse osmosis membranes have higher blocking rates of not only divalent ions, but also monovalent ions, a large amount of reverse osmosis membranes are used for seawater desalination and in the field of electronic industry, in which ultrapure water for washing semiconductors is required.

In the methods using a reverse osmosis membrane, the lactic acid-containing solution is filtered through the reverse osmosis membrane to allow permeation of water into the permeate side of the membrane, while retaining lactic acid in the feed side of the membrane, thereby concentrating lactic acid. Preferred examples of the reverse osmosis membrane include composite membranes having a cellulose acetate polymer as a functional layer (which may be hereinafter referred to as cellulose acetate reverse osmosis membranes) and composite membranes having a polyamide functional layer (which may be hereinafter referred to as polyamide reverse osmosis membranes). Here, examples of the cellulose acetate polymer include organic acid esters of cellulose such as cellulose acetate, cellulose diacetate, cellulose triacetate, cellulose propionate, and cellulose butyrate. These may be used individually, or two or more of these may be used as a mixture or a mixed ester. Examples of the polyamide include linear polymers and cross-linked polymers constituted by aliphatic and/or aromatic diamine monomers. Examples of the form of the membrane that may be used as appropriate include flat membranes, spiral-wound membranes, and hollow fiber membranes.

Specific examples of the reverse osmosis membrane include polyamide reverse osmosis membrane modules manufactured by Toray Industries, Inc., such as SU-710, SU-720, SU-720F, SU-710L, SU-720L, SU-720LF, SU-720R, SU-710P, SU-720P, SU-810, SU-820, SU-820L, SU-820FA, TM800, TM800C, TM800A, TM800H, TM800E, and TM800L; cellulose acetate reverse osmosis membranes manufactured by the same manufacturer, SC-L100R, SC-L200R, SC-1100, SC-1200, SC-2100, SC-2200, SC-3100, SC-3200, SC-8100, and SC-8200; NTR-759HR, NTR-729HF, NTR-70SWC, ES10-D, ES20-D, ES20-U, ES15-D, ES15-U, and LF10-D, manufactured by Nitto Denko Corporation; RO98pHt, R099, HR98PP, and CE4040C-30D, manufactured by Alfa-Laval; "GE Sepa", manufactured by GE; and BW30-4040, TW30-4040, XLE-4040, LP-4040, LE-4040, SW30-4040, and SW3OHRLE-4040, manufactured by FilmTec Corporation.

The concentration with a reverse osmosis membrane is carried out under pressure. The filtration pressure is preferably 1 MPa to 8 MPa since, when the filtration pressure is less than 1 MPa, the membrane permeation rate may be low, while when the filtration pressure is more than 8 MPa, the membrane may be damaged. When the filtration pressure is 1 MPa to 7 MPa, the membrane permeation flux is high so that the lactic acid-containing solution can be efficiently concentrated. The filtration pressure is most preferably 2 MPa to 6 MPa in view of reducing the possibility of damaging the membrane. In a lactic acid-containing solution at a low concentration, a method using a reverse osmosis membrane is especially preferred in view of the cost.

In the concentration using an evaporator, the lactic acid concentration in the solution can be increased by treatment of the lactic acid-containing solution under heat and/or reduced pressure for removal of water and low boiling components into the vapor side. When lactic acid is treated at a high temperature for a long time, oligomerization of lactic acid may occur, leading to a decrease in the yield in the later-described distillation step. The temperature and the residence time are therefore preferably reduced as much as possible. A film evaporator is preferably employed since, by treating the lactic acid-containing solution under reduced pressure using it, both the heating temperature and the residence time can be reduced.

It is especially preferred to carry out the combination of concentration using a reverse osmosis membrane and concentration using an evaporator, from the viewpoint of reducing the input energy and reducing the production of lactic acid oligomers.

Lactic acid in the lactic acid-containing solution obtained in Step A is subjected to a step of crystallization (Step B). The method of crystallization of lactic acid in Step B is not limited, and may be carried out by a method which is ordinarily used. Examples of the method include a method in which the lactic acid-containing aqueous solution is cooled to make lactic acid supersaturated (cooling crystallization), a method in which the solvent (water) is evaporated to make lactic acid supersaturated (evaporative crystallization), and a method in which the solvent (water) is evaporated while the lactic acid solution is cooled, thereby concentrating the solution to make lactic acid supersaturated (insulated crystallization). Among the crystallization methods described above, insulated crystallization may be preferably applied since the input of energy to the cooling can be reduced. In the crystallization, a seed crystal(s) may be added. In the crystallization, either batch distillation or continuous distillation may be applied. In industrial-scale production of lactic acid, it is preferred to use a method in which continuous crystallization, that is, continuous supply of the lactic acid-containing solution and continuous extraction of the lactic acid slurry, is carried out.

A solution containing lactic acid crystals obtained in Step B (lactic acid slurry) is subjected to a step of solid-liquid separation into the lactic acid crystals and the mother liquor (Step C). Known solid-liquid separation methods may be applied to the separation of the lactic acid crystals from the residual liquid component (mother liquor). The lactic acid crystals can be recovered by, for example, decantation, centrifugation, or suction filtration using qualitative filter paper.

Although the lactic acid crystals obtained in Step C are highly pure and applicable to uses in which high purity is required, such as uses as a material of polylactic acid, the mother liquor attached to the crystals may be removed by washing with a washing liquid to obtain crystals having even higher purity. From the viewpoint of prevention of dissolution of the produced lactic acid crystals, which leads to a low crystal recovery, the washing liquid is preferably a poor solvent which does not dissolve lactic acid. Such a poor solvent is not limited, and an aqueous lactic acid solution having a lactic acid concentration of about 80 to 100 wt % is preferably used. More preferably, a part of the lactic acid crystals obtained are dissolved in water to prepare an aqueous solution having the above-described concentration, and the prepared solution is used as the washing liquid.

The mother liquor after the collection of crystals in Step C is subjected to a step of circulation to Step B (Step D). In general, lactic acid in an aqueous solution is in a state where monomers and multimers (oligomers) produced by dehydration condensation of monomers are in equilibrium with each other. In particular, in an aqueous solution of lactic acid at a high concentration, multimers are more likely to be formed because the amount of water is small. We discovered that, in the crystallization of lactic acid, since lactic acid has a high solubility in water, the lactic acid concentration is high in the liquid to be supplied to the crystallization step and in the crystallization mother liquor so that accumulation of oligomers occur in the process of continuous recycling the mother liquor to the crystallization step, leading to a decrease in the crystallization yield, which is problematic. The lactic acid-containing solution obtained in the distillation step (Step A) is subjected to the crystallization step (Step B) so that the accumulation of oligomers in the mother liquor in Step D can be suppressed.

In terms of the method in Step D for circulation of the mother liquor to Step B, the mother liquor may be directly returned to the crystallization tank for Step B, or may be joined through the piping connecting the distillation step (Step A) to the crystallization tank. For the purpose of suppressing excessive accumulation of impurities derived by fermentation in the recycle system, a part of the mother liquor may be discharged to the outside of the system in Step D.

The production of lactic acid is described below using the schematic diagram shown in FIG. 1. Those skilled in the art can easily understand that FIG. 1 merely shows a representative example of our method, and that this example can be modified as appropriate within the scope of this disclosure.

The lactic acid-containing solution derived by microbial fermentation is first supplied to an evaporator 1. Lactic acid in the vapor state is produced by the evaporator that is kept in a vacuum state by a vacuum pump, and then condensed by an evaporative partial condenser 2 together with an arbitrary ratio of water, followed by being transferred to an evaporative partial condensate-receiving tank 3. Water and low boiling components, which have not been condensed by the partial condenser, are condensed by an evaporative total condenser 4, and transferred to an evaporative total condensate-receiving tank 5. Subsequently, lactic acid collected in the distillation step (Step A) is supplied from the evaporative partial condensate-receiving tank 3 to a crystallization tank 6 equipped with a stirrer. The pressure inside the crystallization tank is reduced by a vacuum pump, and lactic acid is concentrated by evaporation of water to allow precipitation of lactic acid crystals (adiabatic cooling, Step B). The evaporated water is condensed in a crystallization tank condenser 7, and transferred to a crystallization condensate-receiving tank 8. The slurry containing lactic acid crystals is transferred from the crystallization tank to a crystallization slurry centrifuge 9, and subjected to solid-liquid separation (Step C). The lactic acid crystals, which are the solid component, are removed as a product, and the mother liquor, which is the liquid component, is transferred to a crystallization mother liquor-receiving tank 10. By recycling the mother liquor from the crystallization mother liquor-receiving tank 10 to the crystallization tank 6, the total yield can be increased (Step D).

We also provide a method of producing polylactic acid, which method comprises a step of producing polylactic acid using, as a material, lactic acid obtained by the lactic acid production process described above (Step E).

Examples of the polylactic acid include homopolymers of L-lactic acid units or D-lactic acid units; polylactic acid block copolymers containing a segment composed of poly-L-lactic acid units and a segment composed of poly-D-lactic acid units; and copolymers with monomers other than lactic acid. When the polylactic acid is a copolymer, examples of the monomer units other than lactic acid include glycol compounds such as ethylene glycol, propylene glycol, butanediol, heptanediol, hexanediol, octanediol, nonanediol, decanediol, 1,4-cyclohexanedimethanol, neopentyl glycol, glycerin, pentaerythritol, bisphenol A, polyethylene glycol, polypropylene glycol, and polytetramethylene glycol; dicarboxylic acids such as oxalic acid, adipic acid, sebacic acid, azelaic acid, dodecanedioic acid, malonic acid, glutaric acid, cyclohexanedicarboxylic acid, terephthalic acid, isophthalic acid, phthalic acid, naphthalenedicarboxylic acid, bis(p-carboxyphenyl)methane, anthracenedicarboxylic acid, diphenyl ether dicarboxylic acid, sodium sulfoisophthalic acid, and tetrabutyl phosphonium isophthalic acid; hydroxycarboxylic acids such as glycolic acid, hydroxypropionic acid, hydroxybutyric acid, hydroxyvaleric acid, hydroxycaproic acid, and hydroxybenzoic acid; and lactones such as caprolactone, valerolactone, propiolactone, undecalactone, and 1,5-oxepan-2-one. The amount of the above-described other copolymerization components to be copolymerized is preferably 0 to 30 mol %, more preferably 0 to 10 mol %, with respect to the total monomer components.

As Step E, a common method for production of polylactic acid may be used. More specifically, known examples of the method include the two-step lactide method, in which lactide, which is a cyclic dimer, is first produced using lactic acid as a material, and ring-opening polymerization is then performed; and the single-step direct polymerization method, in which the material is subjected to direct dehydration polycondensation in a solvent. Either production method may be used. When the direct polymerization method is employed, the lactic acid as the material needs to be highly pure. The lactic acid is sufficiently applicable to the direct polymerization method. The solvent to be used for the direct polymerization method is not limited as long as the solvent does not adversely affect the polymerization, and may be water or an organic solvent. Examples of the organic solvent include aromatic hydrocarbons. Examples of the aromatic hydrocarbons include toluene, xylene, naphthalene, chlorobenzene, and diphenyl ether.

When the polylactic acid is produced by the direct polymerization method, the polymerization can be promoted by discharging water produced by the condensation reaction to the outside of the system. The method of its removal to the outside of the system is preferably polymerization under reduced pressure. More specifically, the pressure is preferably not more than 7 kPa, more preferably not more than 1.5 kPa.

The polymerization time can be shortened by using a catalyst for the polymerization reaction. Examples of the catalyst include metals such as tin, zinc, lead, titanium, bismuth, zirconium, germanium, antimony and aluminum and derivatives thereof. The derivatives are preferably metal alkoxides, carboxylates, carbonates, oxides and halides. Specific examples the derivatives include tin chloride, tin octylate, zinc chloride, lead oxide, lead carbonate, titanium chloride, alkoxytitanium, germanium oxide and zirconium oxide. Among these, tin compounds are preferred, and tin acetate and tin octylate are more preferred.

EXAMPLES

Our method is described below in more detail by way of Examples, but this disclosure is not restricted to the Examples below.

In the Examples, the lactic acid concentration and physical properties of lactic acid crystals were determined by the following measurement methods.

A. Lactic Acid Concentration

The lactic acid concentration in each step was measured by high-performance liquid chromatography (manufactured by Shimadzu Corporation) under the following conditions.

Column: Shim-Pack SPR-H (manufactured by Shimadzu Corporation)

Mobile phase: 5 mM p-toluenesulfonic acid (flow rate: 0.8 mL/min.)

Reaction solution: 5 mM p-toluenesulfonic acid, 20 mM Bis-Tris, 0.1 mM EDTA-2Na (flow rate: 0.8 mL/min.)

Detection method: electric conductivity

Temperature: 45° C.

B. Crystallization Yield

The crystallization yield was calculated according to Equation (1) based on the amount of lactic acid in the liquid supplied to the crystallization step (a mixture of the solution supplied from the distillation step and the crystallization mother liquor) and the amount of lactic acid in the crystals obtained in the crystallization step.

Crystallization yield=100×(amount of lactic acid in crystals)/(amount of lactic acid in supplied liquid in crystallization step)　　(1)

C. Lactic Acid Oligomers in Mother Liquor

The amount of lactic acid oligomers in the crystallization mother liquor was calculated based on the ratio between the peak areas of lactic acid monomers and dimers as determined by high-performance liquid chromatography (manufactured by Shimadzu Corporation) Equation (2) under the assumption that the amount of oligomers corresponds to the amount of dimers, which accounts for a large proportion of the oligomers.

Lactic acid oligomers in the mother liquor=peak area of dimers/peak area of monomers　　(2)

The lactic acid monomers and dimers were analyzed by HPLC under the following conditions.

Column: Phenomenex Synergi 4u Hydro-RP 80A (manufactured by Phenomenex)

Mobile phase: Liquid A, acetonitrile; Liquid B, 0.1% aqueous phosphoric acid solution (gradient conditions: Minute 0 to Minute 5 (Liquid A, 95%; Liquid B, 5%; constant), Minute 5 to Minute 20 (Liquid A, 95%→80%; Liquid B, 5%→20%), Minute 20 to Minute 40 (Liquid A, 80%→30.5%; Liquid B, 20%→69.5%), Minute 40 to Minute 42 (Liquid A, 30.5%→1%; Liquid B, 69.5%→99%), Minute 42 to Minute 45 (Liquid A, 1%; Liquid B, 99%; constant), Minute 45 to Minute 48 (Liquid A, 1%→95%; Liquid B, 99%→5%)); flow rate, 1 mL/min.

Detection method: UV 210 nm

Temperature: 40° C.

Elution time: lactic acid monomers (Minute 3.4 to Minute 4.0), lactic acid dimers (Minute 8.5 to Minute 10.0)

D. Degree of Coloration (APHA) of Lactic Acid Crystals

Pure water was added to the lactic acid crystals to provide 90 wt % aqueous lactic acid solution, and the APHA unit color number was analyzed using a colorimeter (manufactured by Nippon Denshoku Industries Co., Ltd.).

Reference Example 1

Production of Lactic Acid by Batch Fermentation

Lactic acid fermentation using a microorganism was carried out according to Example 4 (pH 3) of WO 2012/147903. The obtained D-lactic acid fermentation broth (D-lactic acid concentration, 40 g/L) was used in the following Examples after removal of the cells by filtration through a microfiltration membrane ("Microza", manufactured by Asahi Kasei Corporation).

Example 1

Production Example of Lactic Acid Using Lactic Acid Fermentation Culture Broth as Material Distillation of Lactic Acid-containing Solution Using a rotary evaporator (manufactured by Tokyo Rikakikai Co., Ltd.), the lactic acid fermentation culture broth obtained in Reference Example 1 was concentrated by evaporation of water under reduced pressure (50 hPa) to obtain 50 wt % lactic acid-containing solution. Subsequently, 1000 g of the concentrated lactic acid-containing solution was continuously supplied to the evaporator at a rate of 56.25 g/h while distillation was performed under a reduced pressure of 600 hPa at 150° C. The first-stage condenser (for partial condensation) was operated at 45° C., and the second-stage condenser (for total condensation) was operated at 2° C. From the first-stage condenser, 462 g of condensed 92 wt % lactic acid-containing solution was obtained. The resulting 92 wt % lactic acid-containing solution was used as the liquid to be supplied to the crystallization step in the following process.

Crystallization of Lactic Acid

As a simulation experiment for the continuous operation including the recycling of the crystallization mother liquor, the following operations (1) to (3) were carried out.

(1) To 154 g of the 92 wt % lactic acid-containing solution collected by the distillation, 0.8g of seed crystals were added, and the resulting mixture left to stand at 25° C. for 2 hours, thereby allowing crystallization of lactic acid.

(2) The resulting slurry containing lactic acid crystals was subjected to solid-liquid separation using Qualitative Filter Paper No. 4 (manufactured by Advantec). The crystals were then subjected to centrifugal filtration using "VIVASPIN" 20 (0.2 µm, manufactured by Sartorius) at 13,000 rpm at 25° C. for 20 minutes to obtain lactic acid crystals. The mother liquor obtained by the use of Qualitative Filter Paper and the centrifugal filtration was used in the recycling.

(3) The mother liquor of (2) and 92 wt % lactic acid-containing solution were mixed together to provide 91 wt % lactic acid-containing solution. After adding 0.005 part by weight of seed crystals to 1 part by weight of the lactic acid-containing solution, the resulting mixture was left to stand at 25° C. for 2 hours, thereby allowing crystallization of lactic acid.

In the first cycle, (1) and (2) were carried out, and, in the second and later cycles, (3) and (2) were repeatedly carried out for evaluation of the lactic acid oligomers in the mother liquor, the crystallization yield, and the degree of coloration of lactic acid crystals in each cycle. The results are shown in Table 1.

Comparative Example 1

Production Example of Lactic Acid without Distillation

Using a rotary evaporator (manufactured by Tokyo Rikakikai Co., Ltd.), 12.5 L of the lactic acid fermentation culture broth obtained in Reference Example 1 was concentrated by evaporation of water under reduced pressure (50 hPa), to obtain 92 wt % lactic acid-containing solution (hereinafter referred to as concentrated lactic acid-containing solution). The resulting 92 wt % concentrated lactic acid-containing solution was used as the liquid to be supplied to the crystallization step in the following process.

Crystallization of Lactic Acid

As a simulation experiment for the continuous operation including the recycling of the crystallization mother liquor, the following operations were carried out.

(1) To 154 g of the 92 wt % concentrated lactic acid-containing solution, 0.8g of seed crystals were added, and the resulting mixture left to stand at 25° C. for 2 hours, thereby allowing crystallization of lactic acid.

(2) The resulting slurry containing lactic acid crystals was subjected to solid-liquid separation using Qualitative Filter Paper No. 4 (manufactured by Advantec). The crystals were then subjected to centrifugal filtration using "VIVASPIN" 20 (0.2 μm, manufactured by Sartorius) at 13,000 rpm at 25° C. for 20 minutes to obtain lactic acid crystals. The mother liquor obtained by the use of Qualitative Filter Paper and the centrifugal filtration was used in the recycling.

(3) The mother liquor of (2) and the 92 wt % lactic acid-containing solution prepared by the concentration using a rotary evaporator were mixed together to provide 91 wt % lactic acid-containing solution. After adding 0.005 part by weight of seed crystals to 1 part by weight of the lactic acid-containing solution, the resulting mixture was left to stand at 25° C. for 2 hours, thereby allowing crystallization of lactic acid.

In the first cycle, (1) and (2) were carried out and, in the second and later cycles, (3) and (2) were repeatedly carried out for evaluation of the oligomers in the mother liquor, the crystallization yield, and the degree of coloration of lactic acid crystals in each cycle. The results are shown in Table 1.

TABLE 1

|  |  | Example 1 | Comparative Example 1 |
|---|---|---|---|
| Cycle 1 | Oligomers in mother liquor | 0.196 | 0.205 |
|  | Crystallization yield (%) | 32.3 | 29.8 |
|  | Degree of Coloration (APHA) | 4 | 20 |
| Cycle 2 | Oligomers in mother liquor | 0.197 | 0.260 |
|  | Crystallization yield (%) | 30.6 | 30.1 |
|  | Degree of Coloration (APHA) | 5 | 28 |
| Cycle 3 | Oligomers in mother liquor | 0.188 | 0.316 |
|  | Crystallization yield (%) | 30.6 | 30.8 |
|  | Degree of Coloration (APHA) | 4 | 39 |
| Cycle 4 | Oligomers in mother liquor | 0.186 | 0.342 |
|  | Crystallization yield (%) | 30.0 | 23.2 |
|  | Degree of Coloration (APHA) | 4 | 45 |
| Cycle 5 | Oligomers in mother liquor | 0.188 | 0.408 |
|  | Crystallization yield (%) | 30.0 | 25.2 |
|  | Degree of Coloration (APHA) | 5 | 57 |
| Cycle 6 | Oligomers in mother liquor | 0.190 | 0.424 |
|  | Crystallization yield (%) | 30.0 | 24.3 |
|  | Degree of Coloration (APHA) | 5 | 71 |

As shown in Table 1, we demonstrated that, by using the lactic acid collected in the distillation step as the liquid to be supplied for the crystallization recycle system, accumulation of lactic acid oligomers in the mother liquor can be suppressed, and high-quality lactic acid crystals with a low degree of coloration can be produced with a stable yield.

Examples 2 and 3

Polymerization Test of Lactic Acid, and Evaluation of Physical Properties of Polylactic Acid To 25 g of lactic acid crystals obtained in the first cycle of Example 1 (Example 2) or the sixth cycle of Example 1 (Example 3), pure water was added to prepare 90 wt % aqueous lactic acid solution. The resulting solution was heated at 160° C. at 800 Pa for 3.5 hours in a reaction vessel equipped with a stirrer to obtain oligomers. Subsequently, 0.02g of tin (II) acetate (manufactured by Kanto Chemical Co., Ltd.) and 0.06g of methanesulfonic acid (manufactured by Wako Pure Chemical Industries, Ltd.) were added to the oligomers, and the resulting mixture heated at 180° C. at 500 Pa for 7 hours, to obtain a prepolymer. The prepolymer was then crystallized by heating in an oven at 120° C. for 2 hours. The obtained prepolymer was pulverized using a hammer mill and passed through a sieve to obtain a powder having an average particle size of 0.1 mm. In the solid phase polymerization step, 25 g of the prepolymer was taken, and fed into an oven to which an oil rotary pump was connected, followed by carrying out vacuum heat treatment. The pressure was set to 50 Pa, and the heating temperature was set to: 140° C. for 10 hours, 150° C. for 10 hours, and 160° C. for 20 hours. The resulting polylactic acid was subjected to analysis of the weight average molecular weight by GPC (manufactured by Tosoh Corporation), analysis of the melting point by DSC (manufactured by SII NanoTechnology Inc.), and analysis of the thermal weight loss rate by TG (manufactured by SII NanoTechnology Inc.) under the same conditions as in Reference Example 3.

Analysis of Weight Average Molecular Weight of Polylactic Acid

The weight average molecular weight (Mw) of the polylactic acid produced by the polymerization is a value calculated in terms of the weight average molecular weight of a standard polymethyl methacrylate measured by gel permeation chromatography (GPC). The GPC measurement was carried out using HLC8320GPC (manufactured by Tosoh Corporation) as a GPC system, and two TSK-GEL SuperHM-M columns (manufactured by Tosoh Corporation) connected in series. The detection was carried out using a differential refractometer. The measurement was carried out under the following conditions: flow rate, 0.35 mL/min.; solvent, hexafluoroisopropanol; injection of 0.02 mL of a solution with a sample concentration of 1 mg/mL.

Analysis of Melting Point of Polylactic Acid

The melting point of the polylactic acid obtained by the polymerization was measured using a differential scanning calorimeter DSC7020 (manufactured by SII NanoTechnology Inc.) The measurement was carried out with 10 mg of the sample under nitrogen atmosphere at a heating rate of 20° C./minute.

Analysis of Thermal Weight Loss Rate of Polylactic Acid

The thermal weight loss rate of the polylactic acid obtained by the polymerization was measured using a thermo gravimetry differential thermal analyzer TG/DTA7200 (manufactured by SII NanoTechnology Inc.). The measurement was carried out with 10 mg of the sample under nitrogen atmosphere at a constant temperature of 200° C. for a heating time of 20 minutes.
The results are shown in Table 2.

Comparative Examples 2 and 3

To 25 g of lactic acid crystals obtained in the first cycle of Comparative Example 1 (Comparative Example 2) or the sixth cycle of Comparative Example 1 (Comparative Example 3), pure water was added to prepare 90 wt % aqueous lactic acid solution. Direct polymerization was carried out under the same conditions as in Examples 2 and 3. As a result, the lactic acid crystals obtained in the sixth cycle of Comparative Example 1 were found to contain a large amount of impurities, and their use for the polymerization was impossible.

TABLE 2

|  | Example 2 | Example 3 | Comparative Example 2 | Comparative Example 3 |
|---|---|---|---|---|
| Molecular weight (Mw/1000) | 253.065 | 257.206 | 128.676 | Unpolymerizable |
| Melting point (° C.) | 167.7 | 167.5 | 154.7 | Unpolymerizable |
| Weight loss rate (%) | 20.9 | 17.43 | 32.64 | Unpolymerizable |

As shown in Table 2, it was demonstrated that, by using the lactic acid collected in the distillation step as the liquid to be supplied for the crystallization recycle system, high-quality lactic acid crystals as well as high-quality polylactic acid can be stably produced.

INDUSTRIAL APPLICABILITY

The lactic acid can be favorably used not only for food and pharmaceuticals, but also as a monomer material for polylactic acid, which is a plastic.

The invention claimed is:

1. A method of producing lactic acid comprising:
   subjecting a lactic-acid containing solution to distillation to collect lactic acid from the vapor side (Step A);
   subjecting the lactic acid obtained in Step A to crystallization (Step B);
   subjecting a lactic acid slurry obtained in (Step B) to solid-liquid separation into lactic acid crystals and a mother liquor containing a lactic acid oligomer (Step C); and
   circulating the mother liquor obtained in Step C to Step B (Step D),
   wherein a mixture of the mother liquor circulated in Step D and the lactic acid obtained in Step A is subjected to crystallization to obtain lactic acid crystals.

2. The method according to claim 1, wherein said lactic acid-containing solution is derived by microbial fermentation.

3. The method according to claim 1, wherein said crystallization in Step B is cooling crystallization, evaporative crystallization, or insulated crystallization.

4. A method of producing polylactic acid comprising:
   producing lactic acid by the method according to claim 1; and
   producing polylactic acid using said lactic acid obtained in said step as a material (Step E).

5. The method according to claim 4, wherein said Step (E) is a step of direct dehydration condensation of said lactic acid.

6. The method according to claim 2, wherein said crystallization in Step B is cooling crystallization, evaporative crystallization, or insulated crystallization.

7. A method of producing polylactic acid comprising:
   producing lactic acid by the method according to claim 2; and
   producing polylactic acid using said lactic acid obtained in said step as a material (Step E).

8. A method of producing polylactic acid comprising:
   producing lactic acid by the method according to claim 3; and
   producing polylactic acid using said lactic acid obtained in said step as a material (Step E).

9. The method according to claim 7, wherein said Step (E) is a step of direct dehydration condensation of said lactic acid.

10. The method according to claim 8, wherein said Step (E) is a step of direct dehydration condensation of said lactic acid.

11. A method of producing lactic acid comprising:
    subjecting a lactic acid-containing solution to distillation to collect lactic acid from the vapor side (Step A);
    partially condensing vapor from the vapor side to produce liquid lactic acid and water, and condensing a remaining portion of the vapor to produce water and low boiling point components (Step A1);
    subjecting the lactic acid obtained in (Step A1) to crystallization (Step B);
    subjecting lactic acid slurry obtained in (Step B) to solid-liquid separation into lactic acid crystals and a mother liquor containing a lactic acid oligomer (Step C); and
    circulating the mother liquor obtained in (Step C) to (Step B) (Step D),
    wherein a mixture of the mother liquor circulated in Step D and the lactic acid obtained in Step A is subjected to crystallization to obtain lactic acid crystals.

12. The method according to claim 11, wherein said lactic acid-containing solution is derived by microbial fermentation.

13. The method according to claim 11, wherein said crystallization in Step B is cooling crystallization, evaporative crystallization, or insulated crystallization.

14. A method of producing polylactic acid comprising:
    producing lactic acid by the method according to claim 11; and
    producing polylactic acid using said lactic acid obtained in said step as a material (Step E).

15. The method according to claim 14, wherein said Step (E) is a step of direct dehydration condensation of said lactic acid.

16. The method according to claim 12, wherein said crystallization in Step B is cooling crystallization, evaporative crystallization, or insulated crystallization.

17. A method of producing polylactic acid comprising:
    producing lactic acid by the method according to claim 12; and
    producing polylactic acid using said lactic acid obtained in said step as a material (Step E).

18. A method of producing polylactic acid comprising:
    producing lactic acid by the method according to claim 13; and
    producing polylactic acid using said lactic acid obtained in said step as a material (Step E).

19. The method according to claim 17, wherein said Step (E) is a step of direct dehydration condensation of said lactic acid.

20. The method according to claim 18, wherein said Step (E) is a step of direct dehydration condensation of said lactic acid.

21. A method of producing lactic acid comprising:
subjecting a solution containing water and lactic acid to distillation to collect lactic acid from the vapor side (Step A), wherein the distillation comprises recovering vaporized lactic acid and a portion of the water in a first-stage condenser and recovering remaining water and low boiling components in a second-stage condenser;
subjecting the lactic acid obtained in Step A to crystallization (Step B);
subjecting the lactic acid slurry obtained in Step B to solid-liquid separation into lactic acid crystals and a mother liquor (Step C); and
circulating the mother liquor obtained in Step C to Step B (Step D),
wherein a mixture of the mother liquor circulated in Step D and the lactic acid obtained in Step A is subjected to crystallization to obtain lactic acid crystals.

* * * * *